(12) United States Patent
Clarot

(10) Patent No.: US 7,754,763 B2
(45) Date of Patent: *Jul. 13, 2010

(54) ORAL COMPOSITION TO REDUCE COLD SYMPTOMS AND DURATION OF SAME

(75) Inventor: Tim Clarot, Phoenix, AZ (US)

(73) Assignee: Zicam, LLC, Scottsdale, AZ (US)

( * ) Notice: Subject to any disclaimer, the term of this patent is extended or adjusted under 35 U.S.C. 154(b) by 635 days.

This patent is subject to a terminal disclaimer.

(21) Appl. No.: 10/837,078

(22) Filed: Apr. 30, 2004

(65) Prior Publication Data

US 2005/0043400 A1  Feb. 24, 2005

Related U.S. Application Data

(60) Provisional application No. 60/467,217, filed on Apr. 30, 2003.

(51) Int. Cl.
*A01N 55/02* (2006.01)
*A01N 59/16* (2006.01)
*A61K 33/32* (2006.01)
*A61F 13/00* (2006.01)

(52) U.S. Cl. ............... 514/494; 424/641; 424/643; 424/434; 514/959

(58) Field of Classification Search ............... 424/434, 424/435, 614, 641, 643; 514/494, 959
See application file for complete search history.

(56) References Cited

U.S. PATENT DOCUMENTS

| | | | |
|---|---|---|---|
| 4,138,477 A | 2/1979 | Gaffar | |
| 4,503,070 A | 3/1985 | Eby, III | |
| 4,684,528 A | 8/1987 | Godfrey | |
| 4,689,214 A | 8/1987 | Niles et al. | |
| 4,758,439 A | 7/1988 | Godfrey | |
| 4,956,385 A | 9/1990 | Eby, III | |
| RE33,465 E | 11/1990 | Eby, III | |
| 5,059,416 A * | 10/1991 | Cherukuri et al. | 424/48 |
| 5,094,845 A | 3/1992 | Vlock | |
| 5,095,035 A | 3/1992 | Eby, III | |
| 5,165,914 A | 11/1992 | Vlock | |
| 5,409,905 A | 4/1995 | Eby, III | |
| 5,897,891 A | 4/1999 | Godfrey | |
| 5,965,610 A | 10/1999 | Modak et al. | |
| 6,037,386 A | 3/2000 | Modak et al. | |
| 6,121,315 A | 9/2000 | Nair et al. | |
| 6,139,864 A | 10/2000 | Durr et al. | |
| 6,169,118 B1 * | 1/2001 | Bilali | 424/463 |
| 6,183,785 B1 | 2/2001 | Westfall | |
| 6,423,300 B1 | 7/2002 | Kleinberg et al. | |
| 6,475,526 B1 | 11/2002 | Smith | |
| 2002/0182267 A1 | 12/2002 | Kleinberg et al. | |
| 2004/0102429 A1* | 5/2004 | Modak et al. | 514/184 |

FOREIGN PATENT DOCUMENTS

WO   WO 03/066001 A   8/2003

OTHER PUBLICATIONS

Eby, GA, "Zinc ion availability—the determinant of efficacy in zinc lozenge treatment of common colds" J Antimicrob Chemother Oct. 1997, 40(4):483-93.

Mossad, SB, et al., "Zinc gluconate lozenges for treating the common cold. A randomized, double-blind, placebo-controlled study." Ann Intern Med Jul. 15, 1996; 125(2):81-8.

Weismann, K, et al., "Zinc gluconate lozenges for common cold. A double-blind clinical trial.", Dan Med Bull Jun. 1990; 37(3):279-81.

Farr, BM, et al., "Two randomized controlled trials of zinc bluconate lozenge therapy of experimentally induced rhinovirus colds." Antimicrob Agents Chemother Aug. 1987; 31(8).

Eby, GA, et al., "Reduction in duration of common colds by zinc bluconate lozenges in a double-blind study." Antimicrob Agents Chemother Jan. 25, 1984(1):20-4.

Mossad, SB, "Effect of zincum gluconicum nasal gel on the duration and symptom severity of the common cold in otherwise health adults." QJM Jan. 2003; 96(1):35-43.

Hirt, M. et al. "Zinc nasal gel for the treatment of common cold symptoms: a double-blind, placebo-controlled trial." Ear Nose Throat J Oct. 2000; 79(10):778-80, 782.

Godfrey, JC et al. "Zinc gluconate and the common cold: a controlled clinical study." J Int Med Res Jun. 1992; 20(3):234-46.

Belongia, EA et al. "A randomized trial of zinc nasal spray for the treatment of upper respiratory illness in adults." Am J Med Aug. 2001; 111(2):103-8.

Turner, RB et al. "Effect of treatment with zinc gluconate or zinc acetate on experimental and natural colds." Clin Infect Dis Nov. 2000; 31(5):1202-8.

Garland, ML et al. "The role of zinc lozenges in treatment of the common cold." Ann Pharmacother Jan. 1998; 32(1):63-9.

Rolla, G et al. "The significance of the source of zinc and its anti-VSC effect." Int Dent J Jun. 2002; 52 Suppl 3:233-5.

McElroy, BH et al. "Effectiveness of zinc gluconate glycine lozenges (Cold-Eeze) against the common cold in school-aged subjects: a retrospective chart review." Am J Ther 2002.

Prasad, AS et al. "Duration of symptoms and plasma cytokine levels in patients with the common cold treated with zinc acetate. A randomized, double-blind, placebo-controlled trial." Ann Itern Med Aug. 15, 2000; 133(4):245-52.

Marshall, S. "Zinc gluconate and the common cold. Review of randomized controlled trials." Can Fam Physician May 1998; 44:1037-42.

* cited by examiner

Primary Examiner—Sreeni Padmanabhan
Assistant Examiner—Umamaheswari Ramachandran
(74) Attorney, Agent, or Firm—Snell & Wilmer L.L.P.

(57) ABSTRACT

An oral spray composition for preventing and/or reducing the symptoms of the common cold including a zinc formulation containing both zinc acetate and zinc gluconate to ensure sustained availability of increased amounts of ionizable zinc.

20 Claims, No Drawings

ORAL COMPOSITION TO REDUCE COLD SYMPTOMS AND DURATION OF SAME

CROSS REFERENCE TO RELATED APPLICATION

This application claims the benefit of provisional application Ser. No. 60/467,217 entitled Composition for Oral Ingestion to Reduce Cold Symptoms and Duration of Same, filed Apr. 30, 2003.

FIELD OF INVENTION

The present invention relates generally to a composition formulated to maintain a therapeutically beneficial ingredient in association with the nasal, oral, and oralpharyngeal membranes to reduce cold symptoms and their duration. More specifically, the present invention relates to an oral spray having a zinc composition for absorption by the nasal, oral, and/or oralpharyngeal membranes to reduce cold symptoms and their duration.

BACKGROUND OF THE INVENTION AND PRIOR ART

The oral and topical administration of zinc and zinc containing compounds have long been utilized in the treatment and prophylaxis of the common cold. For example, a number of patents have been issued to George A. Eby, III which disclose zinc containing compounds for treating the symptoms of, or curing, the common cold.

Eby's U.S. Pat. No. 4,503,070 issued in 1995 discloses the use of a lozenge containing zinc gluconate to reduce the duration of a cold and his U.S. Pat. No. 5,409,905 discloses a composition having a highly ionizable zinc compound which provides sustained release of $Zn^{2+}$ ions. The highly ionizable zinc compound is selected from zinc acetate, zinc propionate, zinc butyrate, zinc betahydroxybutyrate, zinc benzoate, zinc formate, and mixtures thereof while the composition specifically excludes flavor masking amounts of anethole and strong zinc chelators.

U.S. Pat. No. 4,956,385 issued to Eby, III describes the method of applying an ionizable zinc compound other than zinc gluconate to the oral mucosa for treating the common cold. Later, in 1990, Eby's U.S. Pat. No. 4,503,070 was reissued as Re. 33,465 and included claims similar to Eby's '385 patent with the exception that the ionizable zinc compound was specifically identified and defined as being zinc gluconate.

Finally, U.S. Pat. Nos. 5,002,970 and 5,095,035 were issued to Eby, III in 1999 and 1992, respectively, which disclosed oral compositions for releasing zinc ions which included an anethole in an amount to flavor-mask the zinc aftertaste, or a sweet pharmaceutically acceptable carrier. Zinc gluconate, zinc acetate and zinc ascorbate were all identified as individual possibilities for the ionizable zinc compound used with an anethole while zinc acetate was identified as an ionizable zinc compound for use with a sweet pharmaceutically acceptable carrier.

Later, in 1997, two patents were issued to Bryce-Smith, namely U.S. Pat. No. 5,622,724 and U.S. Pat. No. 5,688,531, which disclosed nasal, oral and opthalmological sprays having a dilute solution of unchelated zinc ion for treating cold and allergy symptoms. Zinc sulfate and/or zinc chloride were specifically identified as acceptable selections for the unchelated zinc ion.

Still later, U.S. Pat. No. 6,139,864 was issued to Durr et al. in 2000. The Durr et al. patent describes foods and pharmaceuticals containing zinc and an antimicrobially effective amount of a sugar alcohol mixture. The zinc was identified as being present in the form of zinc gluconate or zinc acetate.

All of these patents disclose zinc compositions that include a single zinc compound as the source of zinc ions. Such compositions are thought to be deficient because the zinc compounds are generally configured to provide only slow release of zinc ions. Accordingly, improved methods and compositions for treating cold symptoms are desired.

SUMMARY OF THE INVENTION

While the way in which the present invention addresses the deficiencies and disadvantages of the prior art is described in greater detail hereinbelow, in general, according to various aspects of the present invention, a method and composition are provided for maintaining a therapeutically beneficial ingredient in association with the nasal, oral, and/or oralpharyngeal membranes to reduce and prevent the common cold and its symptoms. In accordance with various aspects of the present invention, the zinc containing composition is formulated to both increase the concentration of zinc and its ionization potential, and to sustain the release of ionizable zinc. In accordance with various embodiments of the invention, the oral composition includes a zinc formulation containing both zinc gluconate and zinc acetate.

In accordance with various embodiments of the invention, as further described in greater detail below, the oral spray composition comprises a very low viscosity, similar to that of water, and is administered to the oral cavity via a fine spray mist in a dosage of about four squirts, each containing approximately 0.25 milliliters, with the dosage administered approximately every three hours.

In accordance with further embodiments, the oral spray composition includes one or more of a sweetener, flavoring, and a preservative, in addition to a pharmaceutically acceptable carrier.

In accordance with various other aspects of the invention, a system for delivering the composition to the oral cavity is provided. More specifically, a spray applicator is provided for administering spray into the oral cavity.

These and other advantages of the various compositions, methods and systems according to various aspects of the present invention will be apparent to those skilled in the art upon reading and understanding the detailed description below.

DETAILED DESCRIPTION OF EXEMPLARY EMBODIMENTS

In accordance with various aspects of the invention, an oral spray composition is provided which includes two or more zinc salts. The zinc from the zinc salts is desirably freely available, i.e. non-chelated and in an ionizable form, to ensure that it is biologically available and can be readily adsorbed. When administered to the oral cavity via a fine spray mist, the oral spray composition containing the zinc salts will produce a biological electrical circuit from the mouth, through the oral membranes, the oralpharyngeal membranes, and into the nasal membranes. This positive ionic flow of readily ionizable zinc that can be adsorbed into the mucosal membranes is capable of binding to viral ICAM-1 receptors in the nasal passages and inhibits rhinovirus from binding to and infecting nasal mucosal cells.

The oral spray composition of the present invention reduces the presence and/or duration of symptoms associated with the common cold including, but not limited to, headaches, sore throat, runny and/or congested nose, and coughs. More particularly, the oral spray composition of the present invention functions to treat infections associated with those viruses typically recognized as causing common colds. The oral spray of the present invention is preferably used from any time when an individual first notices any signs of a cold up until when the symptoms have cleared.

In a preferred embodiment of the present invention, the composition contains a zinc salt in an amount of about 2 to 6 weight percent of the composition.

In another preferred embodiment of the present invention, the zinc formulation contains both zinc gluconate and zinc acetate, and preferably comprises about 2 to 6 weight percent of the oral spray composition. Moreover, in such a preferred embodiment, zinc gluconate preferably comprises about 2 to 4 weight percent of the oral spray composition and zinc acetate preferably comprises about 0.2 to 2.0 weight percent of the oral spray composition.

In accordance with various aspects of this embodiment, zinc gluconate is present in an amount of about 32 to about 35 mg/ml, preferably about 33.4 mg/ml, and the zinc acetate is present in am amount of about 3 to about 6, preferably about 3.3 mg/ml. Additionally, the combination of the zinc salts provides about 3 to about 7 mg/ml of free ionic zinc, and preferably about 6.1 mg/ml of free ionic zinc.

In accordance with the present invention, the oral spray composition also includes a pharmaceutically acceptable carrier. The pharmaceutically acceptable carrier may include any suitable fluid or liquid such as, for example, purified water, or the like. Preferably, the pharmaceutically acceptable carrier comprises purified water in an amount of about 84.16 to 88 weight percent of the oral spray composition.

The oral spray composition may also include a stabilizer such as glycerin, or the like which functions to keep the zinc in its ionic form. In a preferred embodiment, the stabilizer includes glycerin present at a concentration of about 0.8 to 1.2 weight percent of the oral spray composition, and preferably at about 1.0 weight percent of the oral spray composition. Glycerin as the preferred stabilizer also functions to add a small amount of flavoring to the oral spray composition.

A sweetener and flavor enhancers may also be included in the oral spray composition. Sweeteners may include fructose, dextrose, sucrose or the like. Non-artificial sweeteners work best with a preferred embodiment including fructose in an amount of about 8 to 15 weight percent of the oral spray composition, and preferably at about 10 weight percent of the oral composition. A variety of flavorings may be used, preferably in the form of a stable extract. Alcohol containing forms of flavorings are not preferred. One preferred embodiment of the oral spray composition includes a flavor enhancer, such as peppermint, for example, in an amount of about 0.5 to 2.0 weight percent of the oral spray composition, and preferably at about 1 weight percent of the oral composition.

In accordance with another aspect of the present invention, a preservative may be added to the oral composition to facilitate stability of the various ingredients. Any suitable preservative may be used in accordance with the present invention such as, for example, benzalkonium chloride, benzyl alcohol, and disodium EDTA. Preferably, the preservative includes a 50% solution of benzalkonium chloride admixed into the oral composition at a concentration of about 0.01 to 0.02 percent by weight, and preferably about 0.015 percent by weight.

The composition of the present invention is preferably delivered to the oral cavity through the mouth by way of a fine spray mist. The method includes the steps of obtaining an oral composition in accordance with the present invention for delivery into the oral cavity. The method further includes the step of applying the oral composition to the oral cavity with a spray applicator. Practitioners will appreciate that any suitable applicator may be used. In accordance with a preferred embodiment, the applicator is available from Pfeiffer of America, 12 Roszel Road, Suite C-104, Princeton, N.J. 08540 as Item #63922. This applicator is configured to hold about 120 metered 0.25 ml doses, of the composition.

The composition may be delivered to an individual in any suitable dosage. In accordance with one embodiment of the invention, the oral spray applicator is configured to supply a unit dose of about 0.25 mls of composition to the individual each time a pump associated with the spray applicator is activated (0.25 mls/spray). Preferably, the composition is delivered by applying about 4 sprays in the mouth approximately every 3 hours during waking hours until the cold symptoms have subsided.

EXAMPLES

The Examples set forth below are illustrative of various aspects of certain preferred embodiments of the present invention. The compositions, methods and various parameters reflected therein are intended only to exemplify various aspects and embodiments of the invention, and are not intended to limit the scope of the claimed invention.

Example 1

An exemplary oral spray composition for delivering an active zinc compound to the oral cavity to reduce the presence and duration of cold symptoms is prepared by admixing the following ingredients:

| Component | Function | Amount % w/w |
|---|---|---|
| Zinc Gluconate, USP | Active Substance | 3.34 |
| Zinc Acetate Dihydrate, USP | Active Substance | 0.44 |
| Glycerin Oral Solution, USP | Stabilizer | 1.00% |
| Fructose, USP | Sweetener | 10.00% |
| Peppermint Flavor, GRAS | Flavor Enhancer | 1.00% |
| Benzalkonium Chloride (50% solution), NF | Preservative | 0.015% |
| Purified Water, USP | Diluent/Carrier | 84.2% |

Example 2

Another exemplary oral spray composition for delivering an active zinc compound to the oral cavity is prepared by admixing the following ingredients:

| Component | Function | Amount % w/w |
|---|---|---|
| Zinc Gluconate, USP | Active Substance | 3.34 |
| Zinc Acetate Dihydrate, USP | Active Substance | 0.44 |
| Glycerin Oral Solution, USP | Stabilizer | 1.00% |
| Fructose, USP | Sweetener | 10.00% |
| Mint Flavor | Flavor Enhancer | 1.00% |
| Benzalkonium Chloride (50% solution), NF | Preservative | 0.015% |
| Purified Water, USP | Diluent/Carrier | 84.2% |

The above compositions include about 33.40 mg/ml of zinc gluconate and about 4.40 mg/ml of zinc acetate to provide approximately 6.10 mg/ml of free ionic zinc for adsorption.

An oral spray composition for reducing the severity and duration of symptoms of the common cold has been presented. The oral spray is delivered by way of a fine spray mist through the use of a spray applicator. The zinc formulation included in the oral spray contains zinc or a zinc combination which functions to increase the zinc concentration and the ionization potential of zinc, and to sustain the availability of ionizable zinc for adsorption into the oral, oralpharyngeal, and/or nasal membranes.

The present invention has been described above with reference to exemplary embodiments and examples. It should be appreciated that the particular embodiments shown and described herein are illustrative of the invention and its best mode and are not intended to limit in any way the scope of the invention as set forth in the claims. Those skilled in the art having read this disclosure will recognize changes and modifications may be made to the exemplary embodiments without departing from the scope of the present invention. For example, artisans will recognize that reference to oral, oralpharyngeal, and nasal membranes includes any interior surface of the oral and nasal cavities permitting delivery of an active substance, such as the zinc formulation, to the body, including the epithelial layer of the membranes or mucous of the epithelial layer of the membranes. Further, though reference is made both to "substances" and "ingredients", skilled artisans will further appreciate that the two terms can be used interchangeably. Additionally, although certain components were described herein as being included in the oral composition in addition to the zinc formulation and the pharmaceutically acceptable carrier, it should be understood that carrier may be referred to as also including those certain components and that any suitable carrier may be achieved through any number of combination of additives now known or hereinafter devised. Accordingly, these and other changes or modifications are intended to be included to be within the scope of the present invention, as expressed in the following claims.

The invention claimed is:

1. A composition for delivering an active substance to at least one of an oral membrane, an oral pharyngeal membrane and a nasal membrane by administration through the oral cavity, said composition consisting essentially of:
   at least 84 weight percent of a pharmaceutically acceptable liquid carrier;
   about 0.8 to about 1.2 weight percent stabilizer;
   a sweetener;
   about 0.01 to about 0.02 weight percent preservative;
   about 0.5 to about 2 weight percent flavor enhancer; and
   a zinc formulation consisting of at least 2 weight percent zinc gluconate in the composition and about 0.2 to about 2 weight percent zinc acetate in the composition, said zinc gluconate and said zinc acetate ionized in the liquid carrier.

2. The composition of claim 1, wherein in said composition free ionic zinc is present in an amount of about 3 to about 7 mg/ml.

3. The composition of claim 1, wherein said composition is an oral spray.

4. The composition of claim 1, wherein said pharmaceutically acceptable liquid carrier is present in an amount of about 84 to 88 weight percent of said composition.

5. The composition of claim 4, wherein said pharmaceutically acceptable liquid carrier is purified water.

6. The composition of claim 1, wherein said zinc formulation is present in an amount of about 3 to 6 weight percent of said composition.

7. The composition of claim 1, wherein said stabilizer is glycerin.

8. The composition of claim 1 wherein said sweetener is selected from at least one of the following: fructose and dextrose.

9. The composition of claim 1, wherein said preservative is selected from at least one of the following: benzalkonium chloride and benzyl alcohol.

10. A composition for delivering an active substance to at least one of an oral, an oralpharyngeal, and a nasal membrane by administration through the mouth, said composition consisting essentially of:
    at least about 84 weight percent of a pharmaceutically acceptable liquid carrier;
    about 0.8 to about 1.2 weight percent a stabilizer;
    sweetener;
    preservative;
    flavor enhancer; and
    a zinc formulation consisting of than at least 2 weight percent of zinc gluconate and about 0.2 to about 2.0 weight percent of zinc acetate, wherein said zinc gluconate and said zinc acetate are ionized in said pharmaceutically acceptable liquid carrier.

11. The composition of claim 10, wherein in said composition free ionic zinc is present in an amount of about 3 to about 7 mg/ml.

12. The composition of claim 10, wherein said composition is an oral spray.

13. The composition of claim 10, wherein said pharmaceutically acceptable liquid carrier is present in an amount of about 84 to 88 weight percent of said composition.

14. The composition of claim 13, wherein said pharmaceutically acceptable carrier is purified water.

15. The composition of claim 10, wherein said zinc formulation is present in an amount of about 2 to 6 weight percent of said composition.

16. The composition of claim 10, wherein said stabilizer is glycerin.

17. The composition of claim 10 wherein said sweetener is selected from at least one of the following: fructose and dextrose.

18. The composition of claim 10, wherein said preservative is selected from at least one of the following: benzalkonium chloride and benzyl alcohol.

19. The composition of claim 18, wherein said benzalkonium chloride is present in an amount of about 0.01 to about 0.02 weight percent.

20. The composition of claim 10, wherein said flavor enhancer is present in an amount of about 0.5 to about 2 weight percent of said composition.

* * * * *